United States Patent
Brion et al.

Patent Number: 5,294,704
Date of Patent: Mar. 15, 1994

[54] 4,9(11),17(20)-PREGNATRIENE-3-ONES

[75] Inventors: Francis Brion, Gagny; Jean Buendia, Le Perreux Sur Marne; Christian Diolez, Palaiseau; Michel Vivat, Lagny Sur Marne, all of France

[73] Assignee: Roussel-Uclaf, France

[21] Appl. No.: 971,189

[22] Filed: Nov. 4, 1992

Related U.S. Application Data

[62] Division of Ser. No. 885,150, May 18, 1992, Pat. No. 5,187,273.

[30] Foreign Application Priority Data

May 23, 1991 [FR] France .................... 91 06202

[51] Int. Cl.⁵ .................... C07J 7/00; C07J 75/00; C07J 33/00
[52] U.S. Cl. .................... 540/30; 540/34; 552/602
[58] Field of Search ................ 540/7, 30, 34; 552/602

[56] References Cited

U.S. PATENT DOCUMENTS 4,189,430  2/1980  Shephard .................... 260/239.55

FOREIGN PATENT DOCUMENTS

| | | |
|---|---|---|
| 61416 | 9/1982 | European Pat. Off. . |
| 127216 | 12/1984 | European Pat. Off. . |
| 127217 | 12/1984 | European Pat. Off. . |
| 306969 | 3/1989 | European Pat. Off. . |
| 336521 | 10/1989 | European Pat. Off. . |
| 2022590 | 12/1979 | United Kingdom . |

*Primary Examiner*—Marianne M. Cintins
*Assistant Examiner*—Kimberly J. Kestler
*Attorney, Agent, or Firm*—Bierman and Muserlian

[57] ABSTRACT

A process for the production of a compound of the formula

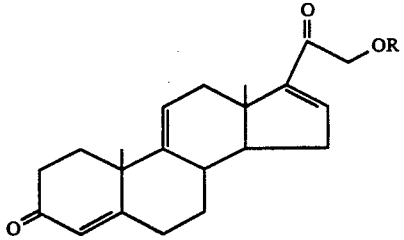

wherein R is an acyl group of 1 to 8 carbon atoms. The compound is formed through an intermediate compound of the formula

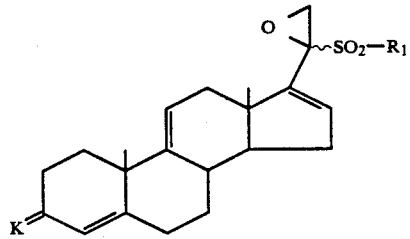

wherein $R_1$ is selected from the group consisting of methyl, phenyl, tolyl, and xylyl and wherein K is a protective group selected from the group consisting of

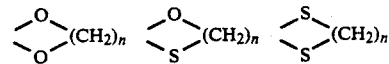

in which n is 2 or 3 and the wavy line means that the group $SO_2$—$R_1$ may have either isomeric form or are mixtures thereof.

7 Claims, No Drawings

4,9(11),17(20)-PREGNATRIENE-3-ONES

PRIOR APPLICATION

This application is a division of U.S. patent application Ser. No. 885,150 filed May 18, 1992, now U.S. Pat. No. 4,187,273.

OBJECTS OF THE INVENTION

It is an object of the invention to provide the novel pregnatriene-3-ones of formula I and a process for their preparation.

It is another object of the invention to provide a novel process for the preparation of $\Delta^{4,9(11),16}$-pregnatriene-3-ones and novel intermediates starting from the compounds of formula I.

These and other objects and advantages of the invention will become obvious from the following detailed description.

THE INVENTION

The novel compounds of the invention have the formula

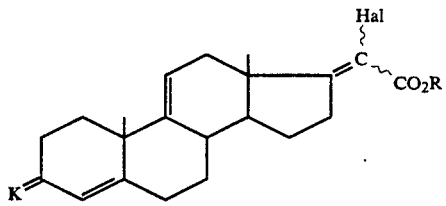

wherein Hal is chlorine or bromine, R is selected from the group consisting of alkyl of 1 to 6 carbon atoms, aralkyl of 7 to 15 carbon atoms and a silylated group, K is a protective group selected from the group consisting of

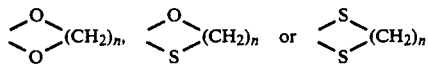

n is 2 or 3 and the wavy lines mean the groups may have either isomer form or are mixtures thereof.

Examples of R are alkyl such as methyl, ethyl, propyl, isopropyl, n-butyl, sec.-butyl, tert.-butyl, pentyl and hexyl and aralkyl such as benzyl and phenethyl and a silylated group such as trimethylsilyl, tert.-butyldimethylsilyl, triphenylsilyl or diphenyltert.-butylsilyl.

A preferred group of compounds of formula I are those wherein Hal is chlorine, R is alkyl of 1 to 3 carbon atoms, K is

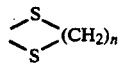

and n is 2 or 3. A specific preferred compound is methyl 20-chloro-3,3-[(1,2-ethanediyl)-bis(thio)]-$\Delta^{4,9(11),17(20)}$-pregnatriene-21-oate.

The novel process of the invention for the preparation of a compound of formula I comprises reacting a compound of the formula

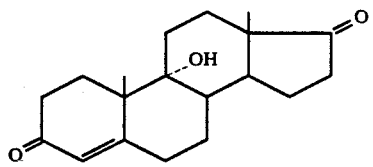

with acetic acid anhydride in the presence of a strong acid, then with an acid hydrolysis agent to obtain a compound of the formula

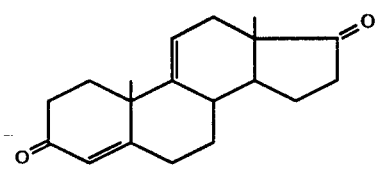

selectively blocking the 3-oxo function by the action of a diol, a thiol or a dithiol of the formula HO—(CH$_2$)$_n$—OH, HO—(CH$_2$)$_n$—SH or HS—(CH$_2$)$_n$—SH in which n is 2 or 3 to obtain a compound of the formula

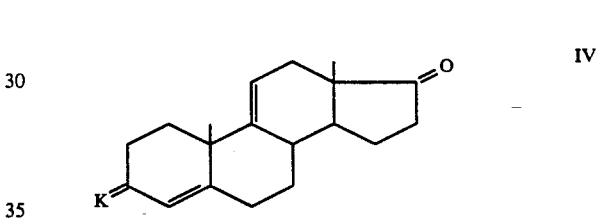

and reacting the latter with a compound of the formula

in which Hal and R are defined as above in the presence of zinc and a Lewis acid to obtain the expected compound of formula I.

The strong acid in the presence of which the acetic acid anhydride is reacted on the product of formula II is preferably P-toluene sulfonic acid, methane sulfonic acid, perchloric acid or hydrochloric acid, hydrobromic acid or sulfuric acid, preferably in catalytic quantity. The hydrolysis agent of the intermediate acetate formed in situ is an aqueous acid, preferably hydrochloric acid, hydrobromic acid or sulfuric acid, or, more preferably formic acid.

The blocking of the 3-ketone is effected with a diol, thiol or dithiol in an acid medium, more particularly ethane dithiol in the presence of concentrated hydrochloric acid or hydrobromic acid in a catalytic quantity, or also in the presence of a Lewis acid such as zinc chloride, titanium tetrachloride or boron trifluoride preferably in the form of the etherate. The Lewis acid used in the reaction of the compound of formula IV with the trihaloacetate is for example, zinc chloride, aluminium chloride, diethyl-aluminium chloride, or, preferably, titanium tetrachloride; preferably carried out in a cyclic ether such as tetrahydrofuran or dioxane.

Another process of the invention for the preparation of a compound of the formula

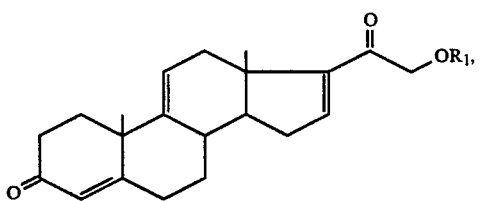

wherein R₁ is acyl of a carboxylic acid of 1 to 8 carbon atoms comprises reacting a compound of formula I in basic medium with a phenol of the formula

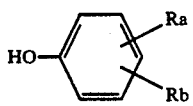

wherein $R_a$ and $R_b$ are individually selected from the group consisting of hydrogen, hydroxy and alkyl and alkoxy of 1 to 4 carbon atoms to obtain a compound of the formula

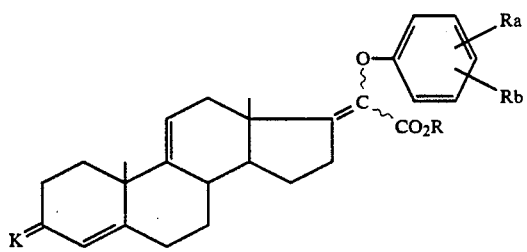

in which K, R, $R_a$ and $R_b$ are defined as above, subjecting the latter to the action of a reducing agent to obtain a compound of the formula

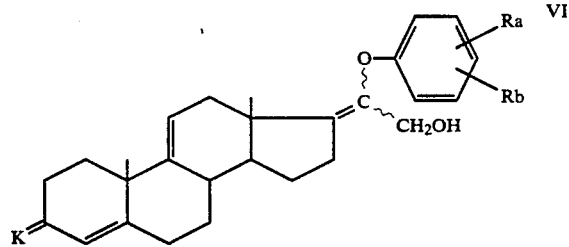

deprotecting the 3-oxo function and then reacting with an epoxidation agent to obtain the corresponding epoxide in 17,20-position and hydrolyzing the latter in an acid medium to obtain a compound of the formula

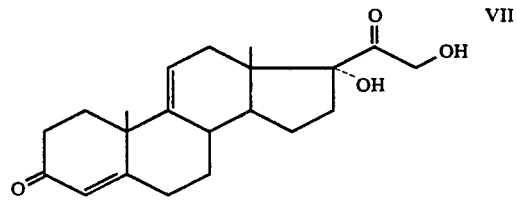

acylating the hyroxy functions to obtain a compound of the formula

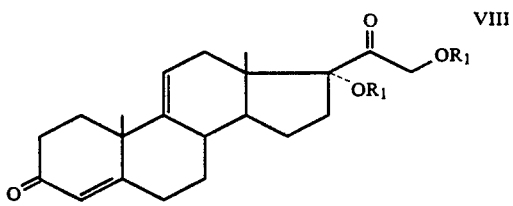

in which R₁ is defined as above, subjecting the latter to the action of an elimination agent of the 17α—OR₁ to obtain the compound of formula A.

The reaction of the phenol with the compound of formula I is carried out in the presence of a base such as an alkali metal or alkaline-earth metal hydroxide or carbonate, in particular sodium, potassium, barium or calcium hydride, alcoholate or alkali amide, in particular sodium, potassium or lithium or also an alkyllithium, in particular butyllithium. The operation is carried out in an organic solvent, for example a ketone such as acetone or methyl ethyl ketone if appropriate mixed with a halogenated solvent such as methylene chloride or with an ether such as dioxane or tetrahydrofuran.

Examples of $R_a$ and $R_b$ as alkyl are ethyl, linear or branched propyl, linear or branched butyl or preferably methyl. Examples of $R_a$ and $R_b$ as alkoxy are ethoxy, linar or branched propoxy, linear or branched butoxy or preferably methoxy. The preferred values for $R_a$ and $R_b$ are hydrogen, hydroxy and methyl.

The reducing agent can he a hydride such as lithium aluminium hydride, diethylsodium-aluminium hydride, diisobutylaluminium hydride or sodium dihydrobis (2-methoxy-ethoxy) aluminate. The operation is carried out, for example, in toluene or tetrahydrofuran. The reducing agent can also be an alkali metal borohydride such as sodium borohydride, catalyzed if appropriate by a lithium salt or lithium borohydride.

The deprotection of the blocked 3-oxo function in the form of a ketal is carried out preferably by the action of an acid in the presence of water. In the case of a dithioketal, it is preferably carried out by the action of iodine in the presence of a base, for example an alkali metal bicarbonate, or by the action of iodine in a catalytic quantity in the presence of an oxidizing agent such as hydrogen peroxide, by the action of methyl iodide, glyoxylic acid, or also metal salts such as mercury or cadmium. The operation can be carried out in a solvent such as a lower alkanol, for example methanol or ethanol, mixed with a halogenated solvent such as methylene chloride, in the presence of water. In the case of an oxathiolane, the deprotection is carried out for example by a mercuric salt such as mercuric chloride in the presence of an acetic acid/potassium acetate buffer at about 100° C., by Raney nickel under the same conditions or by a hot hydrochloric acid acetic acid mixture.

The epoxidation agent can be a peracid such as meta-chloroperbenzoic acid, perphthalic acid, pertungstic acid or hydrogen peroxide used alone or in the presence of hexachloro- or hexafluoroacetone. The epoxidation agent can also be a hydroperoxide such as tert-butyl hydroperoxide used in the presence of vanadium acetylacetonate in a catalytic quantity and the operation is preferably carried out in an organic solvent such as tolune, methylene chloride, chloroform, tetrahydrofuran, dioxane or ethyl acetate.

The hydrolysis of the epoxide in 17,20-position is carried out by the action of an aqueous acid, the acid being a mineral acid such as hydrochloric acid, sulfuric acid or nitric acid in a buffered medium.

The acylation agent is preferably an anhydride or a chloride of formic acid, acetic acid, propionic acid, butyric acid or benzoic acid in the presence of a base, for example an amine such as triethylamine, pyridine or dimethylaminopyridine, an acetate or an alkali metal carbonate. The acylation agent is preferably acetic acid anhydride or acetyl chloride and the acylation in 17 and 21 position can be accompanied by a partial acylation on the enol form in 3-position. The 3-acylated derivative can then be easily hydrolyzed with an acid such as aqueous hydrochloric acid in methylene chloride.

The elimination agent of the $-OR_1$ is a base which can be for example an alkali metal, alkaline-earth metal or amine salt, especially a sodium or potassium salt of the acid corresponding to the acyl radical. The operation is carried out in a polar solvent such as dimethylformamide, dimethylsulfoxide or hexamethylphosphotriamide at a temperature preferably comprised between 90° and 140° C.

Another process of the invention for the preparation of compounds of formula A comprises reacting a compound of formula I in a basic medium with an alkaline sulfinate of the formula $R_2-SO_2Q$ wherein $R_2$ is methyl, phenyl, tolyl or xylyl and Q is alkali metal such as sodium or potassium in the presence of a base to obtain after saponification and decarboxylation a compound of the formula

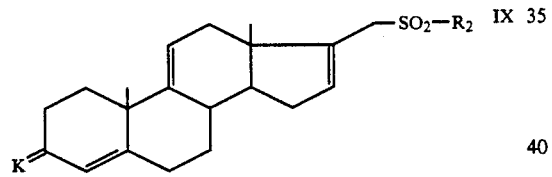

in which K and $R_2$ are defined as above, subjecting the latter to the action of formaldehyde in the presence of a base to obtain a compound of the formula

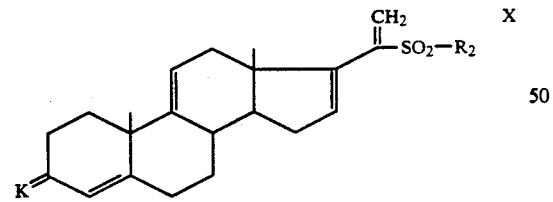

subjecting the latter to the action of an epoxidation agent in an alkaline medium to obtain a compound of the formula

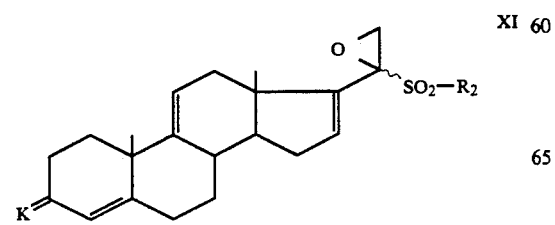

opening the epoxide function in a basic medium and in the presence of $R_1O^\ominus$ ions in which $R_1$ is defined as above to obtain a compound of the formula

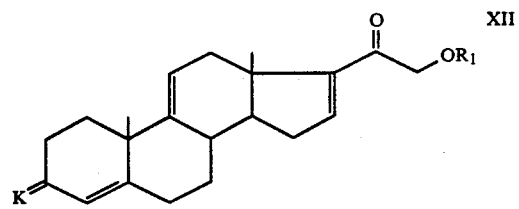

and deprotecting the 3-oxo function to obtain the compound of formula A.

The action of the alkaline sulfinate is carried out in the presence of a basic agent ensuring the reaction conditions for the saponification of the ester. This basic agent can be an alkali metal carbonate such as sodium or potassium carbonate, or an alkali metal hyroxide, such as sodium hydroxide or potassium hydroxide, preferably in excess. The operation is carried out in an aprotic polar solvent, for example dimethylformamide or dimethylsulfoxide and the decarboxylation is carried out preferably at a temperature Close to 100° C., advantageously in a homogeneous phase. The alkaline sulfinate is preferably sodium toluene-sulfinate.

The base in the presence of which the formaldehyde is condensed is a weak base such as a sodium or potassium carbonate or bicarbonate. An alkali metal or alkaline-earth metal hydroxide can also be used and the operation is preferably carried out in dimethylformamide or dimethylsulfoxide at a temperature close to 60° C.

The epoxidation agent is preferably hydrogen peroxide, advantageously carried out in the presence of a base such as alkali metal or alkaline-earth metal hydroxide or carbonate such as sodium, potassium or barium. The epoxidation agent can also be a peracid in an alkaline medium, tert-butyl hydroperoxide catalyzed or not by metals such as vanadium, tungsten or titanium or also oxone. The operation is advantageously carried out in a solvent such as dioxane, tetrahydrofuran or methanol-methylene chloride mixture.

The opening of the epoxide function is carried out using an alkaline, ammonium or amine salt of the $R_1OH$ acid. In a preferred mode of reaction, the operation is carried out with an acetate such as sodium, potassium, ammonium acetate or alkylamines, or an acetic acid-triethylamine mixture. The operation can be carried out in an organic solvent such as dimethylformamide, dimethylsulfoxide, methylethylsulfone or polyethyleneglycol, preferably by slightly heating the reaction medium.

The opening of the epoxide function can also be carried out using a resin of a basic nature and, preferably, a resin in acetate form.

The deprotection of the blocked 3-oxo function is carried out under the conditions mentioned above.

A modification of the process for the preparation of a compound of formula A comprises reacting a compound of formula I with an alkaline sulfinate of the formula $R_2SO_2Q$ in the presence of a base to obtain a compound of the formula

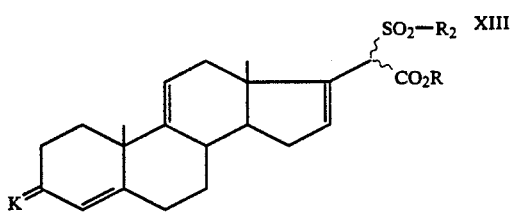

wherein R, R₂ and K are defined as above, reacting the latter with a halogenation agent in the presence of a base, then saponifying and decarboxylating to obtain a compound of the formula

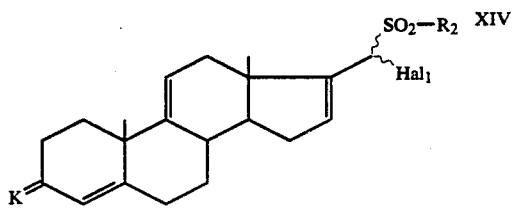

in which $Hal_1$ is halogen, treating the latter with formaldehyde in the presence of a base to obtain a compound of formula XI as defined previously, which is treated as described previously to obtain the desired compound of formula A.

The action of the alkaline sulfinate, which is preferably sodium tolyl sulfinate, is carried out in the presence of a basic agent safeguarding, under the reaction conditions, the ester function. The basic agent can be an alkali metal carbonate or hydroxide, notably sodium or potassium, or also imidazole, morpholine, N-methyl morpholine, triethylamine, piperidine, N-methyl piperidine, pyrrolidine, N-methylpyrrolidine, tripotassium phosphate, alumina, triethanolamine, piperazine, N,N-dimethyl piperazine, hexamethyldisilazane, diazabicyclooctane, dimethylpropylene urea or hexamethylene tetramine. A deficit of base can advantageously be used and the reaction is preferably carried out in an aprotic solvent such as dimethylformamide, dimethylsulfoxide, dimethylacetamide or N-methyl pyrrolidone or in acetonitrile or methylisobutylketone at a temperature from 50° to 120° C.

The halogenation of the compound of formula XIII is carried out by the intermediary of an alkali metal hypohalite, an N-halo-succinimide or a halogen. Sodium hypochlorite or hypobromite is preferably used and $Hal_1$ is therefore preferably chlorine or bromine. The reaction is carried out in the presence of a base such as an alkali metal or alkaline-earth metal hydroxide, notably sodium or potassium hydroxide, or also an alkali metal carbonate or bicarbonate, notably sodium or potassium, and the operation is carried out in a solvent such as an ether like dioxane or tetrahydrofuran or a halogenated solvent, preferably methylene chloride or dichlorethane, at ambient temperature or lower. The operation can be carried out in the presence of a phase transfer catalyst, for example triethylbenzylammonium chloride or tetrabutylammonium bromide.

The saponification and decarboxylation of the ester are preferably carried out by the action of a strong base, for example an alkali metal or alkaline-earth metal hydroxide such as sodium or potassium hydroxide, or of calcium or barium, if appropriate in the presence of an alkanol such as methanol or ethanol and optionally by slightly heating the solution, then by the action of a mineral acid, for example hydrochloric acid, sulfuric acid, hydrobromic acid, nitric acid or also phosphoric acid. The saponification and the decarboxylation can already partially intervene during the halogenation stage of the compound of formula XIII carried out in a basic medium.

The action of formaldehyde on the compound of formula XIV generates in situ a halohydrin which is converted into the desired epoxide and the reaction may be carried out in the presence of a strong base, preferably an alkali metal hydroxide or carbonate such as sodium or potassium, or a tetramethyl or tetraethyl ammonium hydroxide in an organic solvent which is preferably methylene chloride, and in the presence of a phase transfer agent as mentioned above.

Another variation of the process comprises reacting a compound of formula XI with an alkali metal halide to obtain the compound of the formula

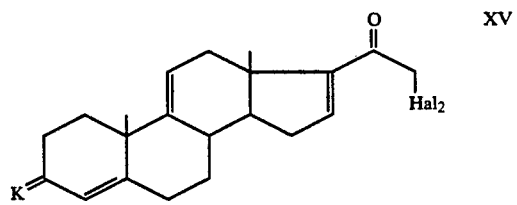

in which $Hal_2$ is chlorine bromine or iodine and K is defined as above, subjecting the latter to the action of an acyloxylation agent in an alkaline medium to obtain the compound of formula XII as defined previously and then the synthesis is continued as described previously.

The alkali metal halide can be a chloride, bromine or iodide of lithium, sodium or potassium. Lithium bromide is preferably used. The reaction is carried out in an organic so.lvent which can be an alkanol, for example methanol, ethanol, isopropanol, or an aprotic polar solvent, for example dimethylformamide or dimethylsulfoxide. The acyloxylation agent is an alkali metal, ammonium or amine salt of the $R_1OH$ acid.

An acetate is preferably used, for example sodium, potassium, ammonium or alkyl amines or an acetic acid - triethylamine mixture and the reaction is carried out in a solvent which can be dimethylformamide, dimethylsulfoxide, acetone, methyl ethyl ketone or methylene chloride. Potassium acetate in dimethylformamide is particulrly preferred and the reaction is carried out in the presence of acetic acid and water. There can also be mentioned potassium acetate in methylene chloride in the presence of a phase transfer catalyst such as one of those mentioned previously and water.

Another modification of the process for the preparation of a compound of formula A comprises reacting-a compound of formula I with a reducing agent to obtain a compound of the formula

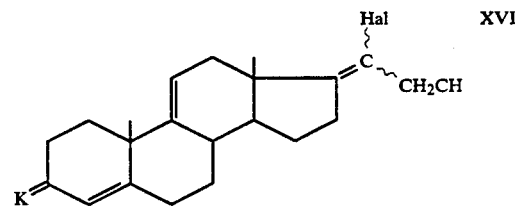

wherein K and Hal are defined as above, reacting the latter with an oxidizing agent to obtain a compound of the formula

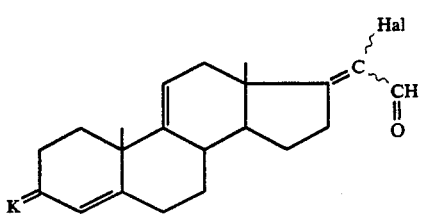  XVII reacting the latter with an acyloxylation agent to obtain a compound of formula XII as defined previously and then the synthesis is continued as described previously. The reduction conditions of the compound of formula I are identical to those specified for the reduction of the compound of formula V.

The oxidizing agent for the compound of formula XVI can be pyridine-$SO_3$ complex by operating in dimethylsulfoxide and advantageously, in the presence of a weak base such as triethylamine or dicyclohexylcarbodiimide, operating in dimethylsulfoxide in the presence of phosphoric acid, or more generally, it can be any oxidizing agent known to a man skilled in the art for oxidizing an alcohol function to an aldehyde function.

The acyloxylation agent for the compound of formula XVII can be one of those mentioned above for the acyloxylation of the compounds of formula XV.

The novel intermediate products of the invention are the compounds of the formula

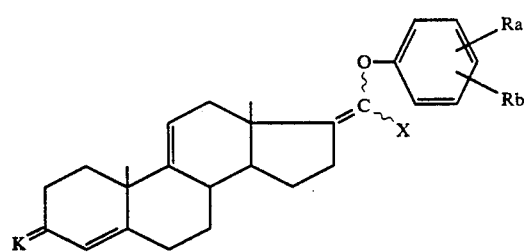  B in which K, $R_a$ and $R_b$ are defined as above and X is $-CH_2OH$ or $-CO_2R$, R being defined as above, the compounds of the formula

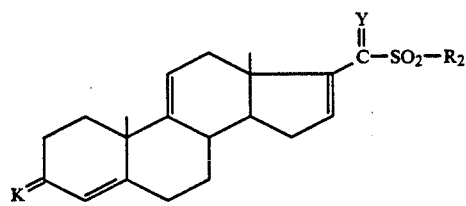  C in which K and $R_2$ are defined as above and $>C=Y$ is $<CH_2$ or $>C=CH_2$ or

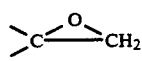

group; the compound of formula XII, the compounds of the formula

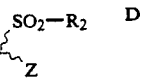  D in which K and $R_2$ are defined as above and Z is $CO_2R$, R being defined as above, or halogen; the compounds of formula XV; the compounds of the formula E in which K and Hal are defined as above and W is $-CH_2OH$ or $-CHO$.

The compounds of formula A are very useful intermediates in the synthesis of various therapeutically active compounds as described, for example, in French Patent No. 1,241,109. The compound of formula II is described in U.S. Pat. No. 3,023,229.

In the following examples, there are described several preferred embodiments to illustrate the invention. However, it is to be understood that the invention is not intended to be limited to the specific embodiments.

EXAMPLE 1

Methyl 20-chloro-3,3-[(1,2-ethanediyl)-bis(thio)]-$\Delta^{4,9(11),17(20)}$-pregnatrien-21-oate STEP A: $\Delta^{4,9}$-Androstadien-3,17-dione 500 g of 9 (1-hydroxy-$\Delta^4$-androstene-3,17-dione and 1 liter of acetic acid anhydride were mixed together under an inert gas and then 50 g of p-toluene sulfonic acid were added at ambient temperature. The mixture was stirred for 3 hours and then 500 ml of formic acid were added slowly at ambient temperature. After stirring for 16 hours, the reaction mixture was poured slowly into 3.5 liters of water and stirring was continued for 2 hours at ambient temperature. After separating, washing with water and drying, 463.9 g of the expected product with a specific rotation of $[\alpha]_D^{20}=212°$ (c=1% in DMF) were obtained.

STEP B: 3,3-[(1,2-ethanediyl)-bis(thio)-$\Delta^{4,9}$-androstadien-17-one 3 g of the product of Step A, 30 ml of methanol and 1 ml of ethane dithiol were mixed together under an inert gas and 0.1 ml of 22°Be hydrochloric acid was added slowly at 20° to 25° C. The mixture was cooled to 0° to +5° C., followed by stirring for one hour. The crystals were separated, washed with methanol, then with water and dried to obtain 3.65 g of the expected product melting at 179° C.

IR Spectrum ($CHCl_3$): Absorption at 1733 and 1405 $cm^{-1}$ (17 keto); Absorption at 1645 $cm^{-1}$ (C=C $\Delta 4$).

STEP C: Methyl 20-chloro-3,3-[(1,2-ethanediyl)-bis(thio)]$\Delta^{4,9(11),17(20)}$-pregnatrien-21-oate 21.8 g of zinc powder were added with stirring under an inert gas to 150 ml of tetrahydrofuran and then 13.7 ml of titanium tetrachloride were added slowly at $-15°$ to $-20°$ C. The mixture was stirred at $-15°$ C. for 15 minutes and then a solution of 30 g of 3,3-[(1,2-ethanediyl)-bis(thio)-$\Delta^{4,9}$-androstadien-17-one and 15 ml of methyl trichloroacetate in 150 ml of tetrahydrofuran were added slowly at $-20°$ C. The mixture was stirred for 10 minutes at $-20°$ C. and then the mixture was allowed to rise to 20° C. After 90 minutes, 150 ml of a water-pyridine mixture (4-1) were added at $+10°$ to $+15°$ C. and the mixture was stirred for one hour. Then the mixture was acidified with a mixture of concentrated hydrochloric acid (50 ml) and ice-cooled water (150 ml) at $+10°$ to $+15°$ C. Extraction was carried out with methylene chloride and after washing with water, drying and evaporating the solvent, 40 g of the crude expected product were obtained. This product was dissolved in methylene chloride and treated with a silica - alumina mixture. After filtering, the solvent was partly evaporated and isopropyl ether was added. The solvent was again partially evaporated, followed by ice-cooling and separating the crystals to obtain 35 g of the expected crystallized product in two lots in the form of a mixture of 2 isomers.

IR Spectrum (CHCl$_3$): Absorption at 1649 cm$^{-1}$ C=C (4.5); 1719-1436 cm$^{-1}$ CO$_2$CH$_3$; 1637-1605 cm$^{-1}$ 2 bands C=C.

NMR Spectrum (CDCl$_3$- 400 MHz ppm): Isomer 1: 18 CH$_3$=0.95 - 19 CH$_3$=1.19 - CO$_2$CH$_3$=3.79 - H$_{11}$=5.42. Isomer 2: 18 CH$_3$=1.00 - 19 CH$_3$=1.18 - CO$_2$CH$_3$=3.81 - H$_{11}$=5.37. H$_4$=5.49 and —CH$_2$S -3.30

EXAMPLE 2

21-acetoxy-$\Delta^{4,9(11),16}$-pregnatriene-3,20-dione

STEP A: Methyl 3,3-[(1,2-ethanediyl)-bis(thio)]-20-phenoxy-$\Delta^{4,9(11),17(20)}$-pregnatrien-21-oate 130 ml of methyl ethyl ketone, 13 g of methyl 20-chloro-3,3-[(1,2-ethanediyl)-bis(thio)]-$\Delta^{4,9(11),17(20)}$-pregnatrien-21-oate, 8.12 g of phenol and 11.95 g of potassium carbonate were mixed together under an inert gas and the mixture was refluxed with stirring for 26 hours. Most of the solvent was distilled off and the residue was taken up in an aqueous solution of sodium bicarbonate, extracted with ethyl acetate, dried and the solvent was evaporated. The product was crystallized from methanol to obtain 6.85 g of the expected product melting at 184° C. The mother liquors were chromatographed on silica, eluting with a methylene chloride cyclohexane mixture (7/3) to obtain another 3.21 g of the expected product, which was made up of a 2-isomer mixture.

NMR Spectrum (CDCl$_3$ - 400 MHz ppm): Isomer 1: 19 CH$_3$=1.13 (s) - 18 CH$_3$=0.87 (s) - CH$_2$—S=3.2 to 3.4 - CO$_2$CH$_3$=3.62 (s) - H$_{11}$=5.32 (d). Isomer 2: 19 CH$_3$=1.20 - 18 CH$_3$=1.10 - CO$_2$CH$_3$=3.66 - H$_{11}$=5.44 (d) - H$_4$=5.29 (s) - H aromatics=6.88.

STEP B: 3,3-[(1,2-ethanediyl)-bis(thio)]-20-phenoxy-$\Delta^{4,9(11),17(20)}$-pregnatriene-21-ol 45 ml of toluene and 8.3 g of the product of Step A were mixed together under an inert gas and the mixture was cooled to 0° to $+5°$ C. 29 ml of a 1.2M solution of diisobutyl aluminium hydride in toluene were added slowly at $+5°$ to $+7°$ C. and, the reaction was stirred at $+5°$ C. for 90 minutes. Then, 1 ml of methanol, 5 ml of 36°Be sodium hydroxide and 20 ml of water were added slowly at $+10°$ to $+15°$ C. After one hour at $+10°$ C., filtration was carried out and the filtrate was washed with water, then with methylene chloride with 10% methanol. The organic phase was decanted, washed with water, dried and the solvent was evaporated. The crude product was taken up in 30 ml of methanol, ice-cooled and separated to obtain 6.67 g of the expected product melting at 228° C.

NMR Spectrum (CDCl$_3$ - 300 MHz ppm): 18 CH$_3$=0.85 (s) 19 CH$_3$=1.13 (s) CH$_2$—S=3.1 to 3.4 - CH$_2$OM=4.16 - H$_{11}$=5.33 - H$_4$=5.47 H aromatics=6.92 (d), 6.98 (t) and 7.26 (t).

STEP C: 20-phenoxy-$\Delta^{4,9(11),17(20)}$-pregnatrien-21-ol-3-one 1.349 g of the product of Step B and 13.5 ml of a methanol methylene chloride - water mixture (5/1/1) were mixed together at ambient temperature and the mixture was stirred for 30 minutes. Then, 54 mg of iodine were added followed by 0.4 ml of 110-volume hydrogen peroxide added over 3 hours. The mixture was stirred for about one hour and was then neutralized by the addition of 0.2N sodium thiosulfate and extracted with methylene chloride. The organic phase was washed with water, dried, and the solvent was evaporated. The crude product was chromatographed on silica, eluting with a cyclohexane - ethyl acetate mixture (6-4) to obtain 1.005 g of the expected product melting at 149° C.

IR Spectrum (CHCl$_3$): Absorption at 1662, 1613 and 866 cm$^{-1}$ (delta 4-3-one); 1596-1491 cm$^{-1}$ ($\phi$-O); 3609 cm$^{-1}$ (free OH); 1596 cm$^{-1}$+shoulder at 1591 cm$^{-1}$ ($\phi$-O-C=C).

STEP D: $\Delta^{4,9(11)}$-pregnadiene-17$\alpha$,21-diol-3,20-dione 1.5 g of the product of Step C and 15 ml of toluene were mixed together under an inert gas and the mixture was cooled to $+5°$ C. 13.8 mg of vanadium acetylacetonate were added and then 0.5 ml of 70% tert-butyl hydroperoxide were added to the solution over 5 minutes at $+5°$ C. The mixture was stirred for 15 minutes at $+5°$ C. and then the solution was allowed to return to ambient temperature and was stirred for one hour. Then, 0.1 ml of tert-butyl hydroperoxide was added and the mixture was stirred for 2 hours 15 minutes. Then, 2 ml of a 0.5M solution of sodium thiosulfate was added followed by stirring for 15 minutes. 6 ml of 2N hydrochloric acid were added and the mixture was stirred for 3 hours. After extracting with methylene chloride with 10% ethanol, the organic phase was washed with water saturated with sodium chloride, dried and evaporated to dryness. The residue was taken up in an ethanol - methylene chloride mixture at reflux and the methylene chloride was driven off, followed by ice-cooling and separating to obtain 1.14 g of product which was treated as above, this time with a methylene chloride - methanol mixture to obtain 1.015 g of the expected product with a melting point >264° C.

NMR Spectrum (CDCl$_3$+deuterized pyridine - 300 MHz ppm): 18 CH$_3$=0.62 (s) - 19 CH$_3$=1.33 (s) - CO—CH$_2$—OH=4.35 (d) and 4.79 (d) - H$_{11}$=5.55 (d) H$_4$=5.74 (s) - Other proton =5.71.

STEP E:
17α,21-diacetoxy-Δ$^{4,9(11)}$-pregnadiene-3,20-dione 4 g of product of Step D, 0.15 g of dimethylaminopyridine, 16 ml of toluene and 5.9 g of acetic acid anhydride were mixed together under an inert gas and the mixture was refluxed for 20 minutes. Then, after cooling, 1 ml of water was added and evaporation to dryness was carried out. The residue was taken up in methylene chloride and 1.2 ml of 22°Be hydrochloric acid were added. The mixture was stirred at ambient temperature for one hour, followed by washing with water, drying and evaporating to dryness. 4.9 g of crude expected product were dissolved in 40 ml of methylene chloride in the presence of alumina and after 10 minutes of stirring, filtration was carried out. About 1 volume of methanol was added and the solution was concentrated hot until crystallization occurred. The crystals were cooled and separated off, washed with methanol and dried to obtain 2.9 g of the expected product.

IR Spectrum (CHCl$_3$) Absence of OH. Absorption at 1735 cm$^{-1}$ (—OAC), 1665 and 1614 cm$^{-1}$ (Δ$^4$- 3 -one)

STEP F: 21-acetoxy-Δ$^{4,9(11),16}$-pregnatriene-3,20-dione 180 ml of dimethylformamide and 3 g of potassium acetate were mixed together under an inert atmosphere and the mixture was refluxed. 60 ml of dimethylformamide were distilled off slowly and the mixture was cooled to 115° C. and 30 g of the product of Step E were introduced. The mixture was then maintained at 115° C. for 3 hours and part of the solvent was distilled off. The mixture was cooled to about 40° C. and, while stirring, 200 ml of water were added. The mixture was stirred for one hour at ambient temperature, and the crystals formed were separated off and dried. The product was taken up in 50 ml of methanol, heated to 45° C., then cooled to 0° C. The crystals were separated off and dried to obtain 16.2 g of the expected product with a specific rotation of $[\alpha]_D^{20} + 166° \pm 2.5°$ (c=1% in DMF).

EXAMPLE 3

21-acetoxy-Δ$^{4,9(11),16}$-pregnatriene-3,20-dione

STEP A:
3,3-[(1,2-ethanediyl)-bis(thio)]-17-[[(4-methylphenyl)-sulfonyl]-methyl]-Δ$^{4,19(11),16}$-androstatriene 12 ml of dimethylformamide, 200 mg of phenol, 300 mg of potassium carbonate, 2 g of sodium tolysulfinate and 2 g of the product of Example 1 were mixed together under an inert gas at ambient temperature. The mixture was heated at 105° C. for 22 hours and then 0.7 g of potassium carbonate and 1.5 ml of water were added. The mixture was taken to 100° C. for one hour and then 10 ml of 2N sodium hydroxide were added. The mixture was maintained at 100° C. for 4 hours and after cooling to 10° C., the mixture was poured slowly into 60 ml of 2N hydrochloric acid. The mixture was stirred for 30 minutes and the product was separated off, taken up in methylene chloride, washed with water and dried. The solvent was evaporated off and the residue was chromatographed on silica, eluting with a cyclohexane ethyl acetate mixture (8-2) and, after crystallization from methanol 1.65 q of the expected product melting at 198° C. were obtained.

IR Spectrum (CHCl$_3$) Absorptions at 1643 cm$^{-1}$ (Δ4), 1598, 1494, 1317, 1303 and 1150 cm$^{-1}$ (tosyl)

NMR Spectrum (CDCl$_3$ - 400 MHz ppm): 18 CH$_3$=0.63 (s) - 19 CH$_3$=1.16 (s) - H$_{11}$=5.37 - N$_4$=5.49 - H$_{16}$=5.77 - H ethanediyl=3.20 to 3.40 (m) - H aromatics=7.33 (d), 7.75 (d) (J=8. Hz) - tosyl CH$_3$=2.45 (s) - H$_{20}$=1.01, 1.44 and 1.77 to 2.42 (m), 3.76 (d) and 3.82 (d) (J=15 Hz).

STEP B:
3,3-[(1,2-ethanediyl)-bis(thio)]-20[(4-methylphenyl)-sulfonyl]-Δ$^{4,9(11),16,20}$-pregnatetraene 1.5 ml of dimethylformamide, 0.3 g of the product of Step A, 0.1 g of potassium carbonate and 0.1 g of paraformaldehyde were mixed together at ambient temperature under an inert gas. The mixture was stirred for 20 hours, then taken to bout 60° C. for 3 hours. The mixture was cooled to +10° C. and 10 ml of water were added. The mixture was stirred for 30 minutes followed by separation. The crystals were taken up in methylene chloride, dried and the solvent was evaporated off. The residue was chromatographed on silica, eluting with a cyclohexane - ethyl acetate mixture (7-3) to obtain 0.28 g of the expected product.

IR Spectrum (CHCl$_3$): Absence of OH.

NMR Spectrum (CDCl$_3$ - 300 MHz ppm): 18 CH$_3$=0.67 (s) - 19 CH$_3$=1.15 (s) - H$_{11}$=5.34 (m) - H$_4$=5.48 - H ethanediyl=3.20 to 3.40 - H$_{16}$=6.40 (m) - H$_{21}$=5.94 and 6.48 - H aromatics=7.28 (d) and 7.68 (d) - tosyl CH$_3$=2.42 (s).

STEP C:
20-21-epoxy-3,3-[(1,2-ethanediyl)-bis(thio)]-20-[(4methylphenyl)-sulfonyl]-Δ$^{4,9(11),16}$-pregnatriene 2 g of the product of Step B, 12 ml of dioxane and 2 ml of water were mixed together at ambient temperature under an inert gas and 3.23 ml of 2N sodium hydroxide and 0.39 ml of 50% hydrogen peroxide were added simultaneously over one hour at a pH of approx. 11. The mixture was stirred at ambient temperature and, after 2 hours, 0.3 ml of 2N sodium hydroxide and 0.06 ml of 50% hydrogen peroxide were added. Then, after 7 hours, 0.03 ml of 50% hydrogen peroxide was added. After 16 hours at ambient temperature, the reaction medium was poured into water saturated with sodium chloride and extraction was carried out with methylene chloride. The extract was washed with a 0.5M solution of sodium thiosulfate and then with water, dried, and the solvent was evaporated. The residue was chromatographed on silica, eluting with a methylene chloride - hexane mixture (8-2) to obtain 1.55 g of the expected product.

NMR Spectrum (CDCl$_3$- 300 MHz ppm): 18 CH$_3$=0.31 (s) and 0.66 (s) - 19 CH$_3$=1,12 (s) and 1.13 (s) - CH$_3$ - $\phi$=2.44 (s) and 2.47 (s) - CH$_2$—O epoxide 2.85 (d) 2.99 (d) and 3.68 (d) - thioketal 3.2 to 3.4 - H$_{11}$=5.19 and 5.32 - H$_4$=5.47 - H$_{16}$=6.29 (m) and 6.39 (m) - $\phi$ SO$_2$=7.33 (m) and 7.73 (m).

STEP D:
21-acetoxy-3,3-[(1,2-ethanediyl)-bis(thio)]-Δ$^{4,9(11),16}$-pregnatrien-20-one 7.5 ml of polyethylene glycol, 1 g of the product of Step C and 0.8 g of sodium acetate were mixed together under an inert gas and the mixture was heated in a bath at 48° C. for 2 hours 45 minutes, then cooled to 0° to +5° C. and poured into ice-cooled water followed by stirring for 30 minutes. After separating, washing the crystals with water and dissolving them in methylene chloride, the solution was dried and brought to dryness. The residue was taken up in methylene chloride and isopropyl ether was added as methylene chloride was driven off. After cooling, the crystals formed were separated off and the filtrate was evaporated to dryness. The residue was chromatographed on silica, eluting with methylene chloride to obtain 0.62 g of the expected product melting at 172° C.

IR Spectrum (CHCl$_3$): Acetate 1748 cm$^{-1}$; Conjugated ketone —C═C 1589 cm$^{-1}$; Δ4 at 1644 cm$^{-1}$.

NMR Spectrum (CDCl$_3$ - 300 MHz ppm): 8 Me=0.85 (s) - 19 Me=1.19 (s) - OAC 2.19 (s)

=4.91, 5.05 (d, J=16) - H$_{11}$=5.45 (m) H$_4$ - 5.50 - H$_{16}$=6.76 (m).

STEP E: 21-acetoxy-Δ$^{4,9(11),16}$-pregnatriene-3,20-dione 1 g of the product of Step D and 12 ml of a methanol - water - methylene chloride mixture (5-1-2) were mixed together at ambient temperature and 0.042 g of iodine were added. The mixture was stirred for 15 minutes and then 0.32 ml of 50% hydrogen peroxide were added over 3 hours. The mixture was stirred for 16 hours and then 6 ml of a 0.2N solution of sodium thiosulfate were added. Extraction was carried out with methylene chloride and the extract was washed with water, dried and evaporated to dryness. The residue was chromatographed on silica eluting with a cyclohexane - ethyl acetate mixture (1-1) to obtain 0. 66 g of the expected product which after crystallization from isopropyl ether melted at 128° C.

IR Spectrum (CHCl$_3$) Absorptions at 1748 cm$^{-1}$ (acetate) and 1684, 1664, 1614 and 1590 cm$^{-1}$ (conjugated ketones).

NMR Spectrum (CDCl$_3$ - 300 MH ppm): 18 CH$_3$=0.89 (s) - 19 CH$_3$=1.36 (s) - H$_{11}$=5.55 (m) - H$_4$=5.76 (d) - H$_{21}$=4.91 and 5.06 (d, J=16 Hz).

EXAMPLE 4

21acetoxy-Δ$^{4,9(11),16}$-pregnatriene-3,20-dione

STEP A: Methyl 3,3-[(1,2-ethanediyl)-bis(thio)]-20-[(4-methylphenyl)-sulfonyl]-Δ$^{4,9(11),16}$-pregnatrien-21-oate 60 ml of dimethylformamide, 25 ml of toluene, 10 g of sodium tolysulfinate, 1 g of phenol, 2 g of sodium carbonate and 0.56 ml of tris[2-(2-methoxyethoxy)-ethyl]-amine were mixed together under an inert gas at ambient temperature. The mixture was refluxed at the temperature of toluene and distilled to eliminate the water. The mixture was cooled to 90° to 100° C. and 10 g of the product of Example 1 were added. The mixture was maintained at about 100° C. for 10 hours and 2 g of sodium tolylsulfinate were added. Heating was continued for 6 hours and the mixture was cooled to 5° to 10° C. and poured slowly into 500 ml of water and ice containing 7 g of monosodium phosphate. Extraction was carried out with methylene chloride and the organic phase was washed with water, dried and evaporated to dryness. The residue was chromatographed on silica, eluting with a cyclohexane - ethyl acetate mixture (90-10) to obtain 9.9 g of the expected product.

IR Spectrum (CHCl$_3$): Absorptions at 1743 cm$^{-1}$ (C═O), 1330, 1148 cm$^{-1}$ (SO$_2$), 1598, 1493 cm$^{-1}$ (aromatics) 1645 cm$^{-1}$ (C═C Δ4).

NMR Spectrum (CDCl$_3$ - 400 MHz ppm): 18 CH$_3$=0.65 (s) - 19 CH$_3$=1.17 (s) -H$_{14}$=1.04 and 1.45 to 2.45 (m) - φ- CH$_3$=2.45 (s) —S—CH$_2$—CH$_2$—S=3.24 to 3.40 (m) - COOCH$_3$=3.66 and 3.72 (2s) - H$_{20}$ =4.53 and 4.55 (2s) - H$_{11}$=5.38 (m) - H$_4$=5.50 (s) - H$_{16}$=6.00 and 6.15 (2s) - H$_3$ and H$_5$=7.33 (d, J=8 Hz) - H$_2$ and H$_6$=7.72 and 7.77 (2d, J=8 Hz).

STEP B:

17-[chloro-[(4-methylphenyl)-sulfonyl]-methyl]-3,3-[(1,2-ethanediyl)-bis(thio)]-Δ$^{4,9(11),16(17)}$-androstatriene 14 ml of dioxane and 6.4 g of the product of Step A were mixed together under an inert gas and a mixture of 13 ml of sodium hypochlorite and 3.4 g of potassium hydroxide in pellet form were added slowly at 20° to 25° C. The mixture was stirred for 90 minutes and then cooled to +10° C. A solution of 1.4 g of sodium thiosulfate with 5H$_2$O in 1.4 ml of water, then 1.4 ml of 32°Be sodium hydroxide were added slowly. The temperature was allowed to rise to 20° to 25° C. and then was taken to 40° C. for 3 hours. After cooling to +10° C., 60 ml of 2N hydrochloric acid were added slowly and after stirring in an ice bath for one hour, the crystals formed were filtered off, washed with water and taken up in methylene chloride. The solution was dried and the solvent was evaporated. The residue was chromatographed on silica, eluting with methylene chloride to obtain 3.73 g of the expected product melting at approx. 250° C.

NMR Spectrum (CDCl$_3$ - 300 MHz ppm): 18 CH$_3$=0.75 and 0.81 - 19 CH$_3$=1.19 (s) - CH$_3$ - φ=2.47 -S—CH$_2$—CH$_2$—S=3.2 to 3.4 - SO$_2$—CH=5.01 and 5.04 - H$_{11}$=5.41 - H$_4$=5.50 - H$_{16}$=6.20 and 6.41 - φ-SO$_2$=7.36 (d) 7.83 (d, resolved).

STEP C:

20,21-epoxy-3,3-[(1,2-ethanediyl)-bis(thio)]-20-[(4-methylphenyl)-sulfonyl]-Δ$^{4,9(11),16}$-pregnatriene 2.7 ml of methylene chloride,. 0.55 g of the product of Step B, 0.2 g of paraformaldehyde, 0.03 g of benzyl triethylammonium chloride and 2 ml of 32°Be sodium hydroxide were mixed together at +10° C. under an inert gas. The mixture was stirred while allowing the temperature to rise to 20° to 25° C. After 2 hours 30 minutes, 0.075 g of paraformaldehyde were added and the mixture was stirred for one hour and then was poured into a saturated aqueous solution of sodium chloride. After extraction with methylene chloride, the extracts were dried and evaporated to dryness. The residue was chromatographed on silica, eluting with.-methylene chloride to obtain 0.462 g of the expected product.

NMR Spectrum (CDCl$_3$- ppm): 18 CH$_3$=0.31 - 0.66; 19 CH$_3$=1.12-1.13; H$_{11}$=5.19 (d) - 5.32; S—CH$_2$—CH$_2$—S=3.24 (m) - 1H - 3.36; H$_4$=5.47; H$_{16}$=6.30 and 6.39; CH$_2$ epoxide=2.86 (d) - 2.99 (d) - 3.68; —CH$_3$=2.44 (d)-2.47 and 7.33 (d) - 7.73 (d).

STEP D: 21-acetoxy-Δ$^{4,9(11),16}$-prenatriene-3,20-dione

Using the procedure of Steps D and E of Example 3, the expected product was obtained.

EXAMPLE 5

21-acetoxy-$\Delta^{4,9(11),16}$-pregnatriene-3,20-dione

STEP A:
21-bromo-3,3-[(1,2-ethanediyl)-bis(thio)]-$\Delta^{4,9(11),16}$-pregnatrien-20-one 1.55 g of the product of Step C of Example 4 and 8 ml of methylene chloride were mixed together under an inert gas and 0.95 g of lithium bromide, then 0.18 ml of methanol were added to the mixture at $-1°/+1°$ C. The mixture was stirred at $1°$ to $+1°$ C. for 7 hours and then 6 ml of water were added at $22°$ C. maximum. After stirring for 10 minutes, the organic phase was decanted and washed with water. Then, it was decolored with activated charcoal and dried to obtain a chloromethylenic solution of the expected product which was used in this form for the following step. A sample of the product obtained by evaporation of the solvent was isolated for analysis.

NMR Spectrum (CDCl$_3$ - 300 MHz ppm): 18 CH$_3$=0.85 (s) - 19 CH$_3$=1.20 (s)-thioketal 3.2 to 3.4 CO—CH$_2$—X=4.17 - H$_{11}$=5.46 - H$_4$=5.50 - H$_{16}$=6.83 (m).

STEP B:
21-acetoxy-3,3-[(1,2-ethanediyl)-bis(thio)]-$\Delta^{4,9(11),16}$-pregnatrien-20-one About 9.5 ml of the 21-bromo product of Step A in solution in methylene chloride were evaporated to half its volume and then 4 ml of dimethylformamide were added. Distillation of the methylene chloride was continued and then 0.8 g of potassium acetate, 0.08 ml of acetic acid and 0.04 ml of water were added to the suspension under an inert gas at about $25°$ C. The mixture was stirred at $25°$ C. for one hour and then was heated at about $60°$ C. for one hour. Then, 1.4 ml of water were introduced slowly and the mixture was cooled to $20°$ C. The crystals were separated off, washed with water - dimethylformamide mixture and dried to obtain 1.54 g of the expected product, identical to that obtained in Step D of Example 3 and being able to be purified as described in said example.

STEP C: 21-acetoxy-$\Delta^{4,9(11),16}$-pregnatriene-3,20-dione

Using the procedure of Step E of Example 3, the expected product was obtained.

EXAMPLE 6

21-acetoxy-$\Delta^{4,9(11),16}$-pregnatriene-3,20-dione

STEP A:
20-chloro-3,3-[(1,2-ethanediyl)-bis(thio)]-$\Delta^{4,9(11),17(20)}$-pregnatriene-21-ol 100 ml of toluene and 6 g of the product of Example 1 were mixed together under an inert gas and the mixture was cooled to $-20°$ C. 38 ml of diisobutylaluminium hydride were introduced slowly and the mixture was stirred for one hour. Then, 3 ml of methanol, and 50 ml. of water were added slowly and the mixture was stirred for 30 minutes. 2N hydrochloric acid was added, and extraction was carried out with ethyl acetate. The organic phase was washed with water, dried and evaporated to dryness. The residue was impasted in 20 ml of isopropyl ether, ice-cooled, filtered and the product was dried to obtain 5.113 g of the expected product melting at $198°$ C.

NMR Spectrum (CDCl$_3$ - 300 mHz ppm): 18 CH$_3$=0.88 and 0.90 - 19 CH$_3$=1.18 (s) - H$_{11}$=5.40 (m) and 5.49 (m) - —S—CH$_2$—CH$_2$—S=3.2 to 3.4 - H$_4$=5.5 - CH$_2$OH - 4.19 (m) - 4.27 (dd) and 4.40 (dd).

STEP B:
20-chloro-3,3-[(1,2-ethanediyl)-bis(thio)]-$\Delta^{4,9(11),17(20)}$-pregnatrien-21-ol 1 g of the product of Step A, 6 ml of dimethylsulfoxide and 3.3 ml of triethylamine were mixed together at ambient temperature under an inert gas and after 15 minutes, 1.47 g of a pyridine-SO$_3$ complex was added slowly while maintaining the temperature at $+20°$ to $+22°$ C. The mixture was stirred at this temperature for 16 hours and the reaction medium was poured into a mixture of 15 ml of 2N hydrochloric acid and 20 ml of ice-cooled water. The mixture was stirred for 30 minutes and the insoluble part was separated off, washed with water and taken up in methylene chloride. The organic solution was dried and the solvent was evaporated. The residue was chromatographed on silica, eluting with a cyclohexane - ethyl acetate mixture (8-2) to obtain after crystallization from 5 ml of isopropyl ether, 0.622 g of the expected product melting at $230°$ C.

NMR Spectrum (CDCl$_3$ - 300 MHz ppm): 18 CH$_3$=0. 99 (s) - 1.08 (s); 19 CH$_3$=1.20 (s) - H$_{11}$=5.44 (m); —S—CH$_2$CH$_2$S=3.2 to 3.4 (m); H$_4$=5.52 (s); H$_{of}$ $_{CHO}$ 973 (s) - 9.91 (s); H$_{16}$ and others=1.40 to 2.95 (m).

STEP C:
21-acetoxy-3,3-[(1,2-ethanediyl)-bis(thio)]-$\Delta^{4,9(11),16}$-pregnatrien-20-one 10 ml of dimethylsulfoxide and 0.7 g of sodium acetate were mixed together under an inert gas and the mixture was taken to $60°$ C. 1.2 g of the product of Step B were introduced slowly and the mixture was stirred for 3 hours at $70°$ C. and cooled. 20 ml of water saturated with sodium chloride were added and the mixture was stirred for 30 minutes and separated. The residue was washed with water and taken up in methylene chloride, followed by drying and evaporating the solvent. The residue was chromatographed on silica, eluting with a cyclohexane - ethyl acetate mixture (8-2) to obtain 0.89 g of the expected product which after crystallization from isopropyl ether melted at $183°$ C.

NMR Spectrum (CDCl$_3$ - 300 MHz ppm): 18 CH$_3$=0.85 (s) 19 CH$_3$=1.19 (s) - H$_{11}$=5.45 (d); —S—CH$_2$—CH$_2$—S=3.2 to 3.4; H$_4$=5.50 (s); acetyl CH$_3$=2.19 (s); CH$_2$21=4.91 (d: J=16) - 5.06 (d; J=16).

STEP D: 21-acetoxy-$\Delta^{4,9(11),16}$-pregnatriene-3,20-dione

Using the procedure of Step E of Example 3, the product of Step C was reacted to obtain the expected product.

Various modifications of the compounds and method of the invention may be made without departing from the spirit or scope thereof and it should be understood that the invention is intended to be limited only as defined in the appended claims.

What we claim is:

1. A process for the preparation of a compound of the formula

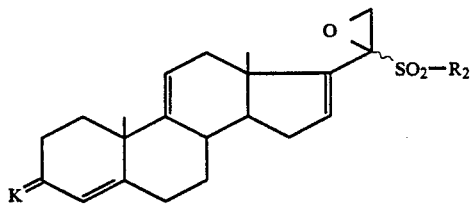

wherein K is a protective group selected from the group consisting

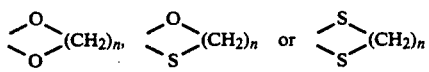

n is 2 or 3, the wavy line means the group may have either isomeric form or is a mixture thereof and $R_2$ is selected from the group consisting of methyl, phenyl, tolyl and xylyl, comprising reacting a compound of the formula

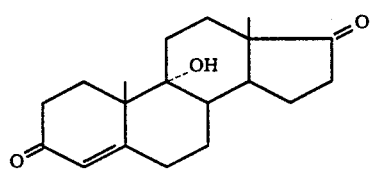

with acetic anhydride in the presence of a strong acid, then with an acid hydrolysis agent to obtain a compound of the formula

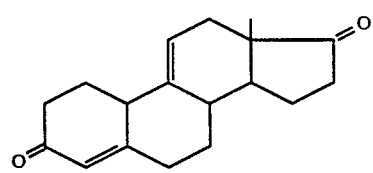

selectively blocking the 3-oxo function with a diol, a thiol or a dithiol of the formula HO—$(CH_2)_n$—OH, HO—$(CH_2)_n$—SH or HS—$(CH_2)_n$—SH, wherein n is defined as above to obtain a compound of the formula

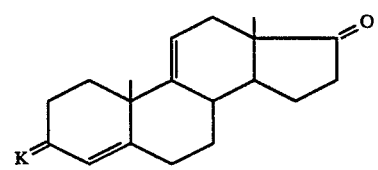

wherein K is defined as above, reacting the latter with a compound of the formula $Hal_3C$—$CO_2R$ wherein Hal is chlorine or bromine and R is selected from the group consisting of alkyl of 1 to 6 carbon atoms, aralkyl or 7 to 15 carbon atoms and a silylated group, in the presence of zinc and a Lewis acid, to obtain a compound of the formula

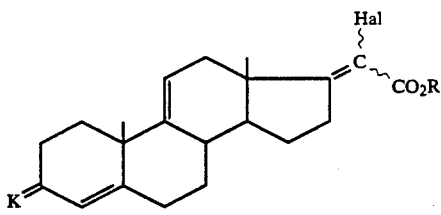

reacting the latter in the presence of a base with an alkali metal sulfinate of the formula $R_2SO_2Q$ wherein $R_2$ is defined as above and Q is an alkali metal, to obtain a compound of the formula

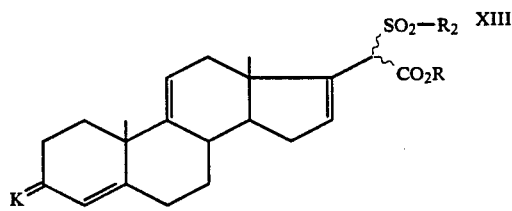

in which R, $R_2$ and K are defined as above, reacting the latter with a halogenation agent in the presence of a base, saponifying and decarboxylating the product to obtain a compound of the formula

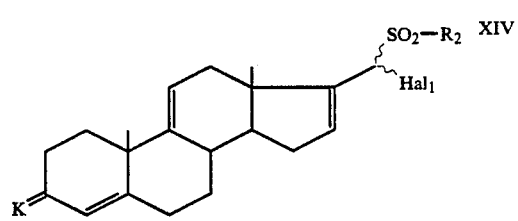

in which $Hal_1$ is halogen, reacting the latter with formaldehyde in the presence of a base to obtain the compound of formula XI.

2. The process of claim 1 wherein the strong acid in the presence of which the acetic anhydride is reacted on the compound of formula II is p-toluene sulfonic acid, the acid hydrolysis agent is formic acid, the blocking agent of the 3-oxo function is ethane dithiol in the presence of a catalytic quantity of concentrated hydrobromic or hydrochloric acid and the Lewis acid is titanium tetrachloride.

3. The process of claim 1 wherein the alkali metal sulfinate is sodium toluene sulfinate and the halogenation agent is sodium hypochlorite or sodium hypobromite.

4. The process of claim 1 further comprising opening the epoxide function of the compound of formula XI in a basic medium and in the presence of $R_1O$ ions, in which $R_1$ is acyl of 1 to 8 carbon atoms to obtain a compound of the formula

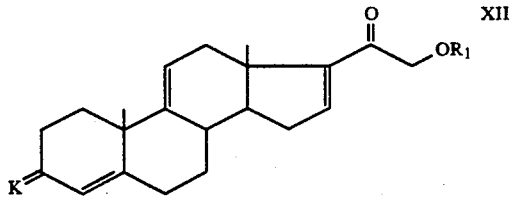

the 3-oxo function of which is deprotected to obtain the compound of formula A

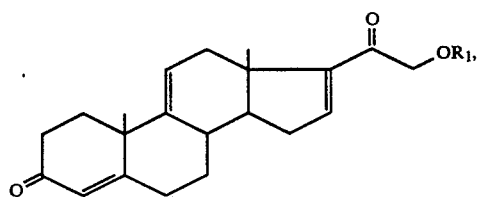

5. The process of claim 4, wherein the opening of the epoxide is carried out in the presence of acetate ions.

6. The process of claim 1, further reacting the compound of formula XI with an alkali metal halide to obtain a compound of the formula

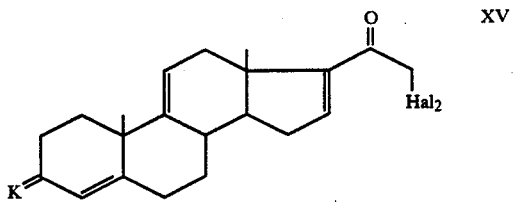

in which $Hal_2$ is chlorine, bromine or iodine and K is defined as in claim 1, subjecting the latter to the action of an acyloxylation agent in an alkaline medium to obtain the compound of formula XII as defined in claim 4 and then the synthesis is continued as described in claim 4.

7. The process of claim 6 wherein the alkali metal halide is lithium bromide and the acyloxylation agent is potassium acetate.

* * * * *